United States Patent
Hirose et al.

(10) Patent No.: US 7,122,696 B2
(45) Date of Patent: Oct. 17, 2006

(54) PROCESSES FOR PREPARATION OF N-PROTECTED-β-AMINO ALCOHOLS AND N-PROTECTED-β-AMINO EPOXIDES

(75) Inventors: Naoko Hirose, Kanagawa (JP);
Tomoyuki Onishi, Kanagawa (JP);
Daigaku Hideura, Kanagawa (JP);
Yasuyuki Otake, Kanagawa (JP);
Kunisuke Izawa, Kanagawa (JP)

(73) Assignee: Ajinomoto Co., Inc., Tokyo (JP)

( * ) Notice: Subject to any disclaimer, the term of this patent is extended or adjusted under 35 U.S.C. 154(b) by 163 days.

(21) Appl. No.: 10/432,353

(22) PCT Filed: Nov. 30, 2001

(86) PCT No.: PCT/JP01/10476

§ 371 (c)(1),
(2), (4) Date: Nov. 24, 2003

(87) PCT Pub. No.: WO02/44136

PCT Pub. Date: Jun. 6, 2002

(65) Prior Publication Data

US 2004/0220417 A1    Nov. 4, 2004

(30) Foreign Application Priority Data

Nov. 30, 2000 (JP) .............................. 2000-365536
Feb. 26, 2001 (JP) .............................. 2001-051109
Mar. 14, 2001 (JP) .............................. 2001-072364

(51) Int. Cl.
*C07C 261/00* (2006.01)
(52) U.S. Cl. ................................................ 560/132
(58) Field of Classification Search ............... 560/129, 560/155, 157, 170, 179, 172, 184, 226
See application file for complete search history.

(56) References Cited

U.S. PATENT DOCUMENTS 6,605,732 B1 * 8/2003 Malik et al. ................. 549/514

FOREIGN PATENT DOCUMENTS

| CA | 2 325 919 | 8/2000 |
|---|---|---|
| EP | 0691 345 | 1/1996 |
| EP | 703209 | 3/1996 |
| EP | 774453 | 5/1997 |
| EP | 0 827 943 | 3/1998 |
| EP | 969000 | 1/2000 |
| EP | 1 050 532 | 11/2000 |
| EP | 1 052 257 | 11/2000 |
| JP | 2000-319235 | 11/2000 |
| JP | 2001-39940 | 2/2001 |
| WO | 00/43357 | 7/2000 |

* cited by examiner

*Primary Examiner*—Thurman K. Page
*Assistant Examiner*—Karl Puttlitz
(74) *Attorney, Agent, or Firm*—Oblon, Spivak, McClelland, Maier & Neustadt, P.C.

(57) ABSTRACT

Herein are disclosed a process for increasing in purity, or purifying, an N-protected-β-aminoalcohol which process comprises (i) adding water to a polar organic solvent in which an N-protected-β-aminoalcohol such as a (2R,3S)- or (2S,3R)-3-tert-butoxycarbonylamino-1-halo-2-hydroxy-4-phenylbutane or the like, or (ii) crystallizing such an N-protected-β-aminoalcohol from a diol or a diol-based mixed solvent, and a process for producing the corresponding N-protected-β-aminoepoxide which process comprises treating, with a base, the thus purity-enhanced N-protected-β-aminoalcohol. Such N-protected-β-aminoalcohols and N-protected-β-aminoepoxides are both useful as synthetic intermediates for medicine compounds, such as, e.g., HIV protease inhibitor and the like.

28 Claims, No Drawings

PROCESSES FOR PREPARATION OF N-PROTECTED-β-AMINO ALCOHOLS AND N-PROTECTED-β-AMINO EPOXIDES

TECHNICAL FIELD

The present invention relates to (a) a process for producing an N-protected-β-aminoalcohol of improved purity (i) by dissolving a certain N-protected-β-aminoalcohol in a polar organic solvent, followed by crystallizing the solute by adding water to the resulting solution (i.e., a process for producing a purity-improved N-protected-β-aminoalcohol, wherein a certain N-protected-β-aminoalcohol is first dissolved in a polar organic solvent, and the resulting solution is then added with water, whereby the N-protected-β-aminoalcohol is precipitated or crystallized in a purer state), or (ii) crystallizing a certain N-protected-β-aminoalcohol from a diol or a diol-based mixed solvent, and (b) a process for producing the corresponding N-protected-β-aminoepoxide by treating an N-protected-β-aminoalcohol produced by the above process, with a base.

BACKGROUND ART

An N-protected-β-aminoalcohol, e.g., such as (2R,3S)-3-tert-butoxycarbonylamino-1-halo-2-hydroxy-4-phenylbutane, (2S,3R)-3-tert-butoxycarbonylamino-1-halo-2-hydroxy-4-phenylbutane, or the like and the corresponding N-protected-β-amino poxide are both useful as synthetic interm diates for medicine compounds, such as, e.g., HIV protease inhibitor, or the like.

Such an N-protected-β-aminoalcohol, e.g., (2R,3S)-3-tert-butoxycarbonylamino-1-chloro-2-hydroxy-4-phenylbutane can be produced, e.g., by reducing (3S)-3-tert-butoxycarbonylamino-1-chloro-4-phenyl-2-butanone.

Likewise, (2S,3R)-3-tert-butoxycarbonylamino-1-chloro-2-hydroxy-4-phenylbutane can be produced, e.g., by reducing (3R)-3-tert-butoxycarbonylamino-1-chloro-4-phenyl-2-butanone.

Reduction of (3S)-3-tert-butoxycarbonylamino-1-chloro-4-phenyl-2-butanone with the use of an appropriate reductant produces, as a by-product, a diastereomer of the target compound, (2S,3S)-3-tert-butoxycarbonylamino-1-chloro-2-hydroxy-4-phenylbutane.

More specifically, it is reported that when it is reduced with tri-tert-butoxy lithium aluminum hydride in ether, (2S,3S)-3-tert-butoxycarbonylamino-1-chloro-2-hydroxy-4-phenylbutane as the undesired diastereomer is formed in an amount of about 1 equivalent per 5 to 8 equivalents of the (2R,3S) diastereomer as the target compound. (Refer to, e.g., the following reports with respect to stereoselective reduction of halomethylketone derivatives: P. Raddats et al; J. Med. Chem., 1991, 34, 11, 3269; A. A. Malik: The 3rd International Conference on Organic Process Research & Development, Development of a Commercial Process for 2S,3S and 2R,3S-epoxides, 10–12th Jul. 2000, Montreal; T. Archibald: Scientific Update Conference Manual, Chiral USA '99, Full Scale Chiral Separations Using SMB, 4th May 1999, San Francisco, Scientific Update; etc.). As might be understood from the above reports, production of (2R,3S)- or (2S,3R)-3-tert-butoxycarbonylamino-1-chloro-2-hydroxy-4-phenylbutane involves serious problems of the impurity diastereomer having to be removed.

In the above reports is disclosed a method of isolating (2R,3S)-3-tert-butoxycarbonylamino-1-chloro-2-hydroxy-4-phenylbutane by silica gel chromatography or high-speed liquid chromatography. These methods, however, may not be industrially preferable, because they need an expensive carrier and a large quantity of solvent, and are complicated ones and time-consuming.

The last report cited above discloses at page 3, that (2R,3S)-3-tert-butoxycarbonylamino-1-chloro-2-hydroxy-4-phenylbutane can only be purified by crystallization upto 94:6 in terms of a ratio of the target compound to its undesired diastereomer (as the impurity), because it has a lower melting point and higher solubility than the undesired diastereomer, and that its purification to a higher level cannot be realized by recrystallization.

Japanese Patent Applicaton Laid-open (Kokai) No. 8-225557 (U.S. Pat. No. 5,481,011) discloses purification and isolation of a halohydrin by crystallization from an appropriate solvent, e.g., ethanol, methanol, isopropanol, toluene, aceton, acetonitrile, water or a mixture thereof. However, the patent document only describes, in the example section, crystallization/isolation of (2S,3S)-N-carbamate-protected-β-aminoalcohol, but is silent as to the effects on the purification and yield, of crystallization of (2R,3S)-3-tert-butoxycarbonylamino-1-chloro-2-hydroxy-4-phenylbutane or the like, which is considered to be difficult to purify.

WO00/43357 discloses purification/isolation of (2R,3S)-3-tert-butoxycarbonylamino-1-chloro-2-hydroxy-4-phenylbutane in the presence of a hydrocarbon-based solvent. However, a highly polar impurity is difficult to remove according to this method.

DISCLOSURE OF THE INVENTION

It is an object of the present invention to provide a process for producing industrially a purity-enhaned (i.e., purity-improved) N-protected-β-aminoalcohol, such as, e.g., a (2R,3S)- or (2S,3R)-3-tert-butoxycarbonylamino-1-halo-2-hydroxy-4-phenylbutane, or the like, and to a process for producing the corresponding N-protected-β-aminoepoxide from such an N-protected-β-aminoalcohol.

The inventors of the present invention have found, after having extensively and intensively studied to attain the above object, that impurities, such as, e.g., diastereomer or highly polar impurities, can be effectively removed from a crude N-protected-β-aminoalcohol, such as, a (2R,3S)-3-tert-butoxycarbonylamino-1-halo-2-hydroxy-4-phenylbutane or a (2S,3R)-3-tert-butoxycarbonylamino-1-halo-2-hydroxy-4-phenylbutane as the optical isomer thereof and thereby the N-protected-β-aminoalcohol of improved or enhanced purity can be obtained by crystallization from a polar organic solvent in which the crude compound has been dissolved, by addition of water, or by crystallization from a diol or a diol-based mixed solvent, and achieved, on the basis of these findings, the process of the present invention for producing an N-protected-β-aminoalcohol.

They have further found that an N-protected-β-aminoalcohol produced by the above process to have an improved purity can be converted into the corresponding N-protected-β-aminoepoxide without being accompanied by impurities difficult to remove, when it is treated with a base, and achieved, on the basis of these findings, the process of the present invention for producing an N-protected-β-aminoepoxide.

Accordingly, the present invention relates to a process for producing a (2R,3S)-N-tert-butoxycarbonyl-β-aminoalco hol or a (2S,3R)-N-tert-butoxycarbonyl-β-aminoalcohol of improved purity which process comprises (i) dissolving, in a polar organic solvent, a (2R,3S)-N-tert-butoxycarbonyl-β-aminoalcohol represented by the following general formula (1):

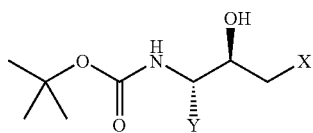
(1)

[wherein, Y represents an alkyl group of 1 to 10 carbon atoms, an aryl group of 6 to 15 carbon atoms or an aralkyl group of 7 to 20 carbon atoms, each of which may have substituent(s); and X represents a halogen atom] or a (2S,3R)-N-tert-butoxycarbonyl-β-aminoalcohol represented by the following general formula (2):

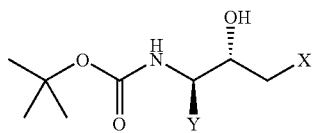
(2)

[wherein, X and Y each represent the same meaning as in the above] and crystallizing the compound represented by the above general formula (1) or (2) from the resulting solution by addition of water, or (ii) crystallizing the compound represented by the above general formula (1) or (2) from a diol or a diol-based mixed solvent.

The present invention also relates to a process for producing a (2R,3S)-N-tert-butoxycarbonyl-β-aminoepoxide represented by the following general formula (3):

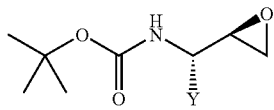
(3)

[wherein, Y represents an alkyl group of 1 to 10 carbon atoms, an aryl group of 6 to 15 carbon atoms or an aralkyl group of 7 to 20 carbon atoms, each of which may have substituent(s)] or a (2S,3R)-N-tert-butoxycarbonyl-β-aminoepoxide represented by the following general formula (4):

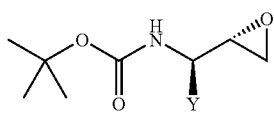
(4)

[wherein, Y represents the same meaning as in the above] which process comprises treating, with a base, the (2R,3S)-N-tert-butoxycarbonyl-β-aminoalcohol or (2S,3R)-N-tert-butoxycarbonyl-β-aminoalcohol of improved purity as produced in accordance with the process of the present invention for producing an N-protected-β-aminoalcohol.

The present invention will be described in greater detail.

A (2R,3S)-N-tert-butoxycarbonyl-β-aminoalcohol represented by the above general formula (1) and (2S,3R)-N-tert-butoxycarbonyl-β-aminoalcohol represented by the above general formula (2) can be obtained by reducing the corresponding halomethyl ketone derivatives, respectively. (2R,3S)-3-tert-butoxycarbonylamino-1-chloro-2-hydroxy-4-phenylbutane, for example, can be obtained by reducing (3S)-3-tert-butoxycarbonylamino-1-chloro-2-hydroxy-4-phenyl-2-butanone, for example.

It is known that a reduction process produces (2R,3S)-3-tert-butoxycarbonylamino-1-chloro-2-hydroxy-4-phenylbutane and (2S,3S)-3-tert-butoxycarbonylamino-1-chloro-2-hydroxy-4-phenylbutane in a produced ratio varying dependently on the type of a reductant used. Therefore, the produced ratio of the impurity diastereomer can be controlled to some extent by selecting an appropriate reductant. (Refer to, e.g., the following reports with respect to stereoselective reduction of halomethylketone derivatives: P. Raddats et al; J. Med. Chem., 1991, 34, 11, 3269; A. A. Malik: The 3rd International Conference on Organic Process Research & Development, Development of a Commercial Process for 2S,3S and 2R,3S-epoxides, 10–12th Jul. 2000, Montreal; T. Archibald: Scientific Update Conference Manual, Chiral USA '9, Full Scale Chiral Separations Using SMB, 4th May 1999, San Francisco, Scientific Update; etc.).

This is the same in connection with the produced ratio of the (2S,3R) form to the (2R,3R) form when (3R)-3-tert-butoxycarbonylamino-1-chloro-4-phenyl-2-butanone is reduced.

The preferable reductants include tri-tert-butoxy lithium aluminum hydride, (+)-B-chlorodiisopinocamphenylborane and tri-sec-butyl boron patassium hydride, and the like. Of these reductants, tri-tert-butoxy lithium aluminum hydride is particularly preferable.

Incidentally, (3S)-3-tert-butoxycarbonylamino-1-chloro-4-phenyl-2-butanone and (3R)-3-tert-butoxycarbonylamino-1-chloro-4-phenyl-2-butanone can be produced by various methods, e.g., by reacting an amino acid ester whose amino group has been protected, with a metallic enolate prepared from an α-haloacetic acid (WO96-23756), followed by decarboxylating, and other known methods disclosed by, e.g., Japanese Patent Application Laid-open (Kokai) No. 6-206857 (EP580402) and WO00-44706.

Next will be described a process for producing an N-protected-β-aminoalcohol represented by the above general formula (1), whose purity has been enhanced, i.e., a (2R,3S)-3-tert-butoxycarbonylaminoalcohol (which may be hereinafter referred to as "the (2R,3S) isomer") or its optical isomer (2S,3R)-3-tert-butoxycarbonylaminoalcohol (which may be hereinafter referred to as "the (2S,3R) isomer").

According to the process of the present invention, the (2R,3S) isomer or the (2S,3R) isomer is dissolved in a polar organic solvent, and then crystallized from the resulting solution by adding water thereto, or each isomer is crystallized from a diol or a diol-based mixed solvent.

First, the crystallization method will be described, wherein the (2R,3S) isomer or the (2S,3R) isomer is dissolved in a polar organic solvent, and then crystallized by adding water to the resulting solution.

First of all, the (2R,3S) isomer or the (2S,3R) isomer is dissolved in a polar organic solvent. As such polar organic solvents useful for the present invention, there may be mentioned those organic solvents compatible with water, e.g., methanol, ethanol, 1-propanol, 2-propanol, tert-butanol, acetone, 2-butanone, acetonitrile, tetrahydrofuran, 2-methoxyethanol, ethylene glycol, 1,3-propanediol and an optional mixture thereof. Of these solvents, methanol and 2-propanol are particularly preferable. Another solvent, e.g., water, may be also present within the limits not harmful to the object of the present invention. A diol and a diol-based mixed solvent, described later, are also included in the inventive polar organic solvents.

Temperature at which the (2R,3S) or (2S,3R) isomer is dissolved in a polar organic solvent is not particularly limited. However, it is preferably −10 to 70° C., more preferably 0 to 40° C. Quantity of such a polar organic solvent to be used is also not particularly limited. However, 2 to 20 ml of the solvent per 1 g of the (2R,3S) or (2S,3R) isomer may be used.

Next, a solution of the (2R,3S) or (2S,3R) isomer dissolved in the organic solvent is added with water, whereby said (2R,3S) or (2S,3R) isomer is caused to crystallize.

Quantity of water to be added is not particularly limited. However, it is preferably 5 to 95% by weight on the polar organic solvent, more preferably 25 to 85%.

Temperature at which the crystallization is carried out is preferably −10 to 70° C., particularly preferably 0 to 40° C. Temperature of water to be added or incorporated for the crystallization is not particularly limited. However, it is preferably the same temperature as the crystallization temperature. How water is incorporated is not particularly limited. However, it is preferably incorporated gradually over a period of from 30 minutes to 4 hours.

The crystallization may be carried out while the solution subjected to crystallization is being stirred or allowed to stand. Seeding of seed crystals can facilitate the crystallization, while or after water is being or has been added, as required. Moreover, the solution may be cooled, as required, while or after water is being or has been added, in such that the crystallization can be carried our at a lower temperature.

When an alcohol, e.g., methanol or the like, is used as the polar organic solvent, the impurity diastereomer has a lower solubility than the target diastereomer to be crystallized in the mixed solvent prepared beforehand by incorporating in or adding to water in the alcohol. According to the process of the present invention, however, where the (2R,3S) or (2S,3R) isomer containing the impurity diastereomer is first dissolved in a polar organic solvent and then crystallized by adding water afterwards, the target (2R,3S) or (2S,3R) isomer is crystallized preferentially, with the result that the impurity diastereomer is left in the mother liquor. Such crude (2R,3S) or (2S,3R) isomer to be purified by the process of the present invention preferably contains the impurity diastereomer at a ratio of 90:10 or less in order to fully realize the effect of removing the impurity diastereomer as one of the effects of the present invention, although the diastereomer ratio varies depending on the kind of the polar organic solvent used.

According to the process of the present invention as described above, the (2R,3S) or (2S,3R) isomer of high purity can be efficiently produced, because it is crystallized out of the solution while leaving behind not only the impurity diastereomer but also highly polar impurities. The crystal separated from the mother liquor may be washed with water, a mixed solvent of water and an alcohol, or an organic solvent, such as, e.g., heptane, hexane, or the like.

Next will be described the crystallization of the (2R,3S) isomer or its optical isomer, the (2S,3R) isomer from a diol or a diol-based mixed solvent. According to the present crystallization, when a diol or a diol-based mixed solvent is employed as the polar organic solvent, crystallization can be carried out without any water being added.

First, the (2R,3S) or (2S,3R) isomer is dissolved in a diol or a diol-based mixed solvent. Temperature at which it is dissolved is not particularly limited. However, it is preferably 40 to 70° C.

As such diols useful for the present invention, there may be mentioned those of 1 to 6 carbon atoms, such as, e.g., ethylene glycol, propylene glycol, butylene glycol, 1,3-propanediol, 1,3-butanediol, 1,4-butanediol, diethylene glycol, and the like of these glycols, ethylene glycol and 1,3-propanediol are particularly preferable. These may be used either individually or in combination of two or more thereof.

The diol-based mixed solvent means a mixed solvent of a diol and water or a mixed solvent of a diol and an organic solvent miscible with the diol. As such a diol, there may be mentioned any one of those named just above. As such organic solvents compatible with a diol, there may be mentioned acetone, 2-butanone, methylisobutylketone, acetonitrile, tetrahydrofuran, methanol, ethanol, 1-propanol, 2-propanol, glycerin, and the like. These may be used either individually or in combination of two or more thereof. The compositional (mixing) ratio of the dial to the other solvent is not particularly limited. However, it is preferably 50 v/v % or more (v/v % means volumetric ratio of the diol in the mixed solvent).

Quantity of a diol or a diol-based mixed solvent to be used is not particularly limited. However, 2 to 20 ml of the solvent per 1 g of the (2R,3S) or (2S,3R) isomer may be used.

It is recommended to carry out the crystallization while the system is being cooled, preferably at 10 to 30° C. The crystallization may be carried out while the solution is being stirred or allowed to stand. Use of seed crystals can facilitate the crystallization process, if required.

In, e.g., ethylene glycol, or the like, among diols or diol-based mixed solvents, the impurity diastereomer has a lower solubility than the target diastereomer to be crystallized. However, th target diastereomer is found to be crystallized preferentially, with the result that the impurity diastereomer is left in the solution. Therefore, a crude (2R,3S) isomer or (2S,3R) isomer to be subjected to the production process (isolation, purification process) of the present invention preferably contains the impurity diastereomer at a ratio of 90:10 or less in order to fully realize the effect of removing the impurity diastereomer as one of the effects of the present invention, although the diastereomer ratio varies depending on the kind of the solvent used.

Like in the one described earlier, the process of the present invention can efficiently produce the (2R,3S) or (2S,3R) isomer of high purity, because it is crystallized out of the solution while leaving behind not only the impurity diastereomer but also highly polar impurities. The crystals separated from the mother liquor may be washed with water, a mixed solvent of water and an alcohol, or an organic solvent, such as, egg., heptane, hexane, or the like, as has been described earlier.

Incidentally, the (2R,3S) or (2S,3R) isomer to be treated or treated by the process of the present invention may be dissolved in a specific solvent before or after it is subjected to the inventive crystallization, whereby the insoluble impurities can be removed. This can remove the impurity diastereomer to a still higher extent.

The preferable solvents for the above purpose include organic compounds, such as, e.g., xylene, toluene, chlorobenzene, n-hexane, n-heptane, cyclohexane, methylcyclohexane, and the like; and a mixed solvent of water and an alcohol, such as, e.g., methanol, ethanol, 2-propanol, or the like. Of these solvents, a mixed solvent of 2-propanol and water, and toluene and xylene are particularly preferable.

The impurity diastereomer is dissolved in the above solvents only sparingly, and can be removed as insoluble matter in a slurried state. Moreover, it may be crystallized after being dissolved in a solvent at above room temperature and then cooled to an appropriate temperature.

Quantity of a solvent to be used is preferably 1 to 50 times of the weight of the target compound to be dissolved therein. Usually, it is dissolved in the solvent with stirring at −20° C. to below the boiling point of the solvent to be used. When xylene, for example, is used as the solvent, it is dissolved at around 35 to 70° C. The resulting solution is preferably filtered while it is still hot to remove the insolubles. When toluene, for another example, is used as the solvent, it is dissolved at around room temperature to −20° C. The resulting solution may be filtered to remove the insolubles. When a mixed solvent of 2-propanol and water is used, the solution is preferably filtered at around 0 to 50° C. to remove the insolubles. It is possible for those who are skilled in the art to determine easily more preferable conditions, as required, for a specific solvent to be used. The impurity diastereomer can be separated as solid by removing the insolubles by filtration or the like.

It is possible to increase the ratio of the target diastereomer to the impurity diastereomer to, e.g., 95:5 or more, or still higher to 98:2 or more by the above procedure before the process of the present invention is carried out.

The (2R,3S) isomer obtained as in the above, can be converted to the corresponding N-protected-β-aminoepoxide represented by the following general formula (3), i.e., (2R,3S)-3-tert-butoxycarbonylaminoepoxide, by treating with a base.

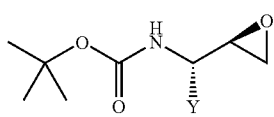

(3)

Likewise, the (2S,3R) isomer can be converted to the corresponding (2S,3R)-3-tert-butoxycarbonylaminoepoxide represented by the following general formula (4), by treating with a base.

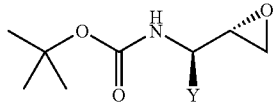

(4)

These reactions are known to those who are skilled in the art, because they are disclosed by, e.g., Japanese Patent Application Laid-open (Kokai) No. 6-206857 (EP580402), and the like.

As such bases, sodium hydroxide, potassium carbonate, and the like are preferably used. As such reaction solvents, ethanol, a mixed solvent of water and ethanol, 2-propanol or acetone, and the like are preferably used. Quantity of the base to be used can be normally 1 to 10 equivalents, preferably 1 to 5 equivalents, per 1 equivalent of the reactant substrate. Reaction temperature can be normally −10 to 80° C., preferably 0 to 60° C. Reaction time is preferably from around 10 minutes to 50 hours. The reaction is allowed to proceed normally with stirring, and on completion, may be terminated by addition with an acid. As such an acid, hydrochloric acid, sulfuric acid, acetic acid, citric acid, an aqueous solution of potassium bisulfate, or the like can be preferably used.

The compound represented by each of the general formulae (3) and (4) is useful as an intermediate for medicine compounds, such as, e.g., HIV protease inhibitor and the like, as has been described earlier.

By the way, X represents a halogen atom such as a chlorine, bromine or the like atom in the above general formulae (1) and (2). Of these atoms, a chlorine atom is preferred for the purpose of the present invention. On the other hand, Y represents an alkyl group, an aryl group or an aralkyl group in the above general formulae (1)–(4). Of these groups, a benzyl group is preferred for the purpose of the present invention.

Accordingly, there may be mentioned as preferred embodiments of the present invention, Embodiment (A): A process for producing (2R,3S)-3-tert-butoxycarbonylamino-1-chloro-2-hydoroxy-4-phenybutane or (2S,3R)-3-tert-butoxycarbonylamino-1-chloro-2-hydoroxy-4-phenybutane, which process comprises (i) adding water to an polar organic solvent in which (2R,3S)-3-tert-butoxycarbonylamino-1-chloro-2-hydroxy-4-phenylbutane represented by the following formula (5):

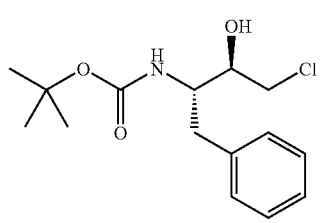

(5)

or (2S,3R)-3-tert-butoxycarbonylamino-1-chloro-2-hydroxy-4-phenylbutane represented by the following formula (6):

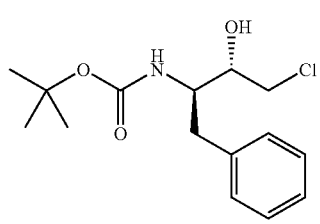

(6)

has been dissolved whereby said (2R,3S)-3-tert-butoxycarbonylamino-1-chloro-2-hydroxy-4-phenylbutane or said (2S,3R)-3-tert-butoxycarbonylamino-1-chloro-2-hydroxy-4-phenylbutane is crystallized, or (ii) crystallizing (2R,3S)-3-tert-butoxycarbonylamino-1-chloro-2-hydroxy-4-phenylbutan represented by the above formula (5) or (2S,3R)-3-tert-butoxycarbonylamino-1-chloro-2-hydroxy-4-phenylbutane represented by the above formula (6) from a diol or a diol-based mixed solvent, and Embodiment (B): A process for producing (2R,3S)-3-tert-butoxycarbonylamino-1,2-epoxy-4-phenylbutane represented by the following formula (7):

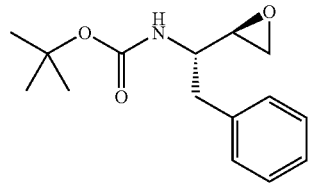

(7)

or (2S,3R)-3-tert-butoxycarbonylamino-1,2-epoxy-4-phenylbutane represented by the following formula (8):

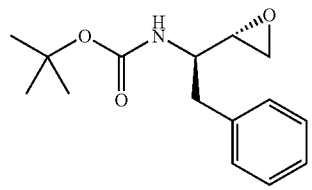

(8)

which process comprises producing (2R,3S)-3-tert-butoxycarbonylamino-1-chloro-2-hydroxy-4-phenylbutane or (2S,3R)-3-tert-butoxycarbonylamino-1-chloro-2-hydroxy-4-phenylbutane in accordance with the above-described production process, and treating, with a base, said (2R,3S)-3-tert-butoxycarbonylamino-1-chloro-2-hydroxy-4-phenylbutane or said (2S,3R)-3-tert-butoxycarbonylamino-1-chloro-2-hydroxy-4-phenylbutane.

BEST MODE FOR CARRYING OUT THE INVENTION

The present invention will be described in more detail with reference to Examples, which by no means limit the present invention, needless to say. The ratios of the target diastereomer to its undesired diastereomer as described in Examples, are all molar ratios.

REFERENCE EXAMPLE 1

Synthesis of (2R,3S)-3-tert-butoxycarbonylamino-1-chloro-2-hydroxy-4-phenylbutane:

In an argon atmosphere, dehydrated diethyl ether (100 mL) was added with tri-tert-butoxy lithium aluminum hydride (4.7 g). The resulting mixture was cooled to 0° C., and then added with (3S)-3-tert-butoxycarbonylamino-1-chloro-4-phenyl-2-butanone (5.0 g), and stirred at 0° C. for 3 hours. The reaction solution was added with 1N hydrochloric acid (37 ml) to terminate the reaction, and then separated into two layers. The organic layer was, after separated, washed with 1N hydrochloric acid and then with saturated saline. The washed organic layer was concentrated in vacuo to remove the solvent, and the residue was added with methanol (23.2 ml) at room temperature, whereby it was dissolved therein. The resulting methanol solution was analyzed by HPLC. It was confirmed that the diastereomer mixture of 3-tert-butoxycarbonylamino-1-chloro-2-hydroxy-4-phenylbutane was produced in a total yield of 92.1%. The production ratio of the target (2R,3S) diastereomer to the impurity (2S,3S) diastereomer was (2R,3S):(2S,3S)=87.4:12.6.

The resulting methanol solution was cooled to 0° C., and added with water (6 ml). After the resulting mixture had been seeded with seed crystals, water (22.2 ml) was added thereto dropwise over a period of 1 hour. The mixture was stirred for 2 hours The crystals formed were filtered, and washed with heptane (15 ml) twice and then with water (25 ml) also twice. The washed crystals were dried, and the (2R,3S)-3-tert-butoxycarbonylamino-1-chloro-2-hydroxy-4-phenylbutane diastereomer was obtained in a yield of 85.4% (4.30 g). The production ratio of the target (2R,3S) diastereomer to the impurity (2S,3S) diastereomer was (2R,3S):(2S,3S)=87.0:13.0 therein.

REFERENCE EXAMPLE 2

Purification of (2R,3S)-3-tert-butoxycarbonylamino-1-chloro-2-hydroxy-4-phenylbutane:

A crude (2R,3S)-3-tert-butoxycarbonylamino-1-chloro-2-hydroxy-4-phenylbutane diastereomer product (21.9 g) as prepared in the same manner as that of Reference Example 1, and containing the (2S,3S) diastereomer at a (2R,3S):(2S,3S) ratio of 84.9:15.1, was added with 2-propanol (49.2 ml) and water (16.4 ml), to be dissolved therein at 70° C. The resulting solution was cooled to 20° C. over a period of 4 hours. Further, it was stirred at 20° C. for 16 hours, and then cooled to 15° C., at which temperature it was stirred for 1 hour. The insolubles produced were removed by filtration. The mother liquor was concentrated to dryness, and the (2R,3S)-3-tert-butoxycarbonylamino-1-chloro-2-hydroxy-4-phenylbutane diastereomer was obtained in a recovery yield of 81.9% (17.9 g). The production ratio of the target (2R,3S) diastereomer to the impurity (2S,3S) diastereomer was (2R,3S):(2S,3S)=98.4:1.6 therein.

EXAMPLE 1

Purification of (2R,3S)-3-tert-butoxycarbonylamino-1-chloro-2-hydroxy-4-phenylbutane (1):

A crude (2R,3S)-3-tert-butoxycarbonylamino-1-chloro-2-hydroxy-4-phenylbutane diastereomer product (0.997 g) as prepared in the same manner as that of Reference Example 2, and containing 0.790 g and 0.013 g of the (2R,3S) and (2S,3S) diastereomers, respectively (therefore, (2R,3S):(2S,3S) ratio being 98.4:1.6, and the (2R,3S) diastereomer purity being 94.2%, as determined by the HPLC area ratio), was added with methanol (4.0 ml) as a polar organic solvent to be dissolved therein at room temperature (20° C.). The resulting solution was added with water (2.5 ml) dropwise over a period of 20 minutes, and then seeded with seed crystals, followed by stirring for 30 minutes. The mixture was cooled from 20° C. to 0° C. over a period of 1 hour, and then stirred for 40 minutes, followed by filtering. The crystals collected by filtering were dried, and the (2R,3S) diastereomer was obtained in a recovery yield of 78.2% (0.618 g). The (2R,3S):(2S,3S) ratio was 100:0, and the (2R,3S) diastereomer purity was 99.4%, as determined by the HPLC area ratio.

$^1$H-NMR(CDCl$_3$, 300 MHz) δppm: 1.38 (s, 9H), 2.91 (dd, J=8.1, 13.2 Hz, 1H), 3.01 (dd, J=7.1, 13.2 Hz, 1H), 3.14 (d, J=4.0 Hz, 1H), 3.53 (s, 1H), 3.55 (d, J=2.3 Hz, 1H), 3.70–3.77 (m, 1H), 3.79–3.89 (m, 1H), 4.88 (bd, 1H), 7.19–7.35 (m, 5H).

Mass spectra m/e: 322 (M+Na$^+$).

$[α]_D^{20}$=−28.3° (c=0.50, CH$_2$Cl$_2$).

EXAMPLE 2

Purification of (2R,3S)-3-tert-butoxycarbonylamino-1-chloro-2-hydroxy-4-phenylbutane (2):

A crude (2R,3S)-3-tert-butoxycarbonylamino-1-chloro-2-hydroxy-4-phenylbutane diastereomer product (1.007 g) as prepared in the same manner as that of Reference Example 2, and containing 0.982 g and 0.017 g of the (2R,3S) and (2S,3S) diastereomers, respectively ((2R,3S):(2S,3S) ratio being 98.3:1.7, and the (2R,3S) diastereomer purity being 97.5%, as determined by the HPLC area ratio), was added with ethylene glycol (5 ml) to be dissolved therein at 60° C. The resulting solution was cooled from 60° C. to 50° C. over a period of 1 hour, and then seeded with seed crystals, followed by stirring for 30 minutes. The mixture was cooled from 50° C. to 20° C. over a period of 3 hours, and then stirred for 2 hours, followed by filtering. The crystals collected by filtering were washed with a 1:1 mixed solution of ethylene glycol and water (3 ml) and water (3 ml) in this order. The washed crystals were dried, and the (2R,3S)-3-tert-butoxycarbonylamino-1-chloro-2-hydroxy-4-phenylbutane diastereomer was obtained in a recovery yield of 67.1% (0.660 g). The (2R,3S):(2S,3S) ratio was 99.94:0.06, and the (2R,3S) diastereomer purity was 99.8%, as determined by the HPLC area ratio.

EXAMPLE 3

Purification of (2R,3S)-3-tert-butoxycarbonylamino-1-chloro-2-hydroxy-4-phenylbutane (3):

A crude (2R,3S)-3-tert-butoxycarbonylamino-1-chloro-2-hydroxy-4-phenylbutane diastereomer product (1.000 g) as prepared in the same manner as that of Reference Example 2, and containing 0.972 g and 0.017 g of the (2R,3S) and (2S,3S) diastereomers, respectively ((2R,3S):(2S,3S) ratio being 98.3:1.7, and the (2R,3S) diastereomer purity being 97.2%, as determined by the HPLC area ratio), was added with 1,3-propanediol (5 ml) to be dissolved therein at 60° C. The resulting solution was cooled from 60° C. to 40° C. over a period of 2 hours, and then seeded with seed crystals. The mixture was cooled from 40° C. to 5° C. over a period of 3 hours and 30 minutes, and then stirred for 2 hours, followed by filtering. The crystals collected by filtering were washed with a 1:1 mixed solution of methanol and water (3 ml). The washed crystals were dried, and the (2R,3S)-3-tert-butoxycarbonylamino-1-chloro-2-hydroxy-4-phenylbutane diastereomer was obtained in a recovery yield of 63.8% (0.620 g). The (2R,3S):(2R,3S) ratio was 100:0, and the (2R,3S) diastereomer purity was 99.5%, as determined by the HPLC area ratio.

EXAMPLE 4

Purification of (2R,3S)-3-tert-butoxycarbonylamino-1-chloro-2-hydroxy-4-phenylbutane (4):

A crude (2R,3S)-3-tert-butoxycarbonylamino-1-chloro-2-hydroxy-4-phenylbutane diastereomer product (1.000 g) as prepared in the same manner as that of Reference Example 2, and containing 0.981 g and 0.016 g of the (2R,3S) and (2S,3S) diastereomers, respectively ((2R,3S):(2S,3S) ratio being 98.4:1.6, and the (2R,3S) diastereomer purity being 98.1%, as determined by the HPLC area ratio), was added with ethylene glycol (4 ml) and 1,4-butanediol (0.6 ml) to be dissolved therein at 60° C. The resulting solution was cooled from 60° C. to 48° C. over a period of 1 hour, and then seeded with seed crystals. The mixture was cooled from 48° C. to 20° C. over a period of 3 hours and then stirred for 2 hours, followed by filtering. The crystals collected by filtering were washed with a 1:1 mixed solution of methanol and water (3 ml). The washed crystals were dried, and the (2R,3S)-3-tert-butoxycarbonylamino-1-chloro-2-hydroxy-4-phenylbutane diastereomer was obtained in a recovery yield of 69.4% (0.686 g). The (2R,3S):(2S,3S) ratio was 100:0, and the (2R,3S) diastereomer purity was 99.5%, as determined by the HPLC area ratio.

EXAMPLE 5

Purification of (2R,3S)-3-tert-butoxycarbonylamino-1-chloro-2-hydroxy-4-phenylbutane (5):

A crude (2R,3S)-3-tert-butoxycarbonylamino-1-chloro-2-hydroxy-4-phenylbutane diastereomer product (1.000 g) as prepared in the same manner as that of Reference Example 2, and containing 0.981 g and 0.016 g of the (2R,33) and (2S,3S) diastereomers, respectively ((2R,3S):(2S,3S) ratio being 98.4:1.6, and the (2R,3S) diastereomer purity being 98.1%, as determined by the HPLC area ratio), was added with ethylene glycon (6 ml), 2-propanol (2.4 ml) and water (1.7 ml) to be dissolved therein at 60° C. The resulting solution was cooled from 60° C. to 30° C. over a period of 3 hours, and then seeded with seed crystals, The mixture was cooled from 30° C. to 20° C. over a period of 1 hour and then stirred for 2 hours, followed by filtering. The crystals collected by filtering were washed with a 1:1 mixed solution of methanol and water (3 ml). The washed crystals were dried, and the (2R,3S)-3-tert-butoxycarbonylamino-1-chloro-2-hydroxy-4-phenylbutane diastereomer was obtained in a recovery yield of 58.2% (0574 g). The (2R, 3S):(2S,3S) ratio was 100:0, and the (2R,3S) diastereomer purity was 99.5%, as determined by the HPLC area ratio.

EXAMPLE 6

Purification of (2R,3S)-3-tert-butoxycarbonylamino-1-chloro-2-hydroxy-4-phenylbutane (6):

A mother liquor (3.68 g) as prepared in the same manner as that of Reference Example 2, ((2R,3S)-3-tert-butoxycarbonylamino-1-chloro-2-hydroxy-4-phenylbutane) and containing 0.982 g and 0.017 g of the (2R,3S) and (2S,3S) diastereomers, respectively ((2R,3S):(2S,3S) ratio being 98.3:1.7, and the (2R,3S) diastereomer purity being 97.9%, as determined by the HPLC area ratio), was heated to 40° C. and added with ethylene glycol (6 ml) and water (1.2 ml). The resulting solution was cooled from 40° C. to 30° C. over a period of 1 hour, and then seeded with seed crystals, followd by stirring for 1 hour. The mixture was cooled from 30° C. to 20° C. over a period of 1 hour, and then stirred for 2 hours, followed by filtering. The crystals collected by filtering were washed with a 1:1 mixed solution of methanol and water (3 ml). The washed crystals were dried, and the (2R,3S)-3-tert-butoxycarbonylamino-1-chloro-2-hydroxy-4-phenylbutane diastereomer was obtained in a recovery yield of 58.5% (0.576 g). The (2R,3S):(2S,3S) ratio was 100:0, and the (2R,3S) diastereomer purity was 99.8%, as determined by the HPLC area ratio.

INDUSTRIAL APPLICABILITY

In the production of N-protected-β-aminoalcohols such as, e.g., (2R,3S)- or (2S,3R)-3-tert-butoxycarbonylamino-1-chloro-2-hydroxy-4-phenylbutane or the like, the impurity diastereomer and highly polar impurities can be efficiently removed according to the present invention, and therefore, purity-enhanced or -improved N-protected-β-aminoalcohols can be obtained. From this purity-enhanced N-protected-β-aminoalcohols (i.e., the N-protected-β-aminoalcohols of enhanced or improved purity) can, in turn, be produced highly pure N-protected-β-aminoepoxides. Accordingly, the production process of the present invention can be a highly productive process for producing synthetic intermediates for medicine compounds, such as, e.g., HIV protease inhibitor, or the like, in the production on an industrial scale.

What is claimed is:

1. A process for producing a (2R,3S)-N-tert-butoxycarbonyl-β-aminoalcohol or a (2S,3R)-N-tert-butoxycarbonyl-β-aminoalcohol, comprising:
crystallizing a compound represented by formula (1) or (2):

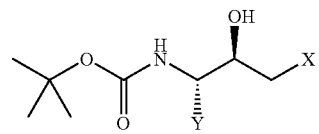
(1)

wherein
Y represents an alkyl group of 1 to 10 carbon atoms, an aryl group of 6 to 15 carbon atoms or an aralkyl group of 7 to 20 carbon atoms, each of which may have substituent(s); and
X represents a halogen atom,

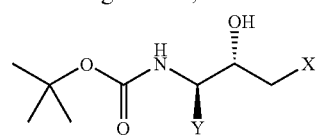
(2)

wherein
X and Y are each as defined above, from a diol or a diol-based mixed solvent.

2. The process of claim 1, wherein the compound represented by formula (1) is crystallized.

3. The process of claim 1, wherein the compound represented by formula (1) is crystallized.

4. A process for producing a (2R,3S)-N-tert-butoxycarbonyl-β-aminoepoxide represented by the following general formula (3):

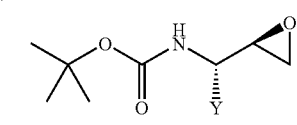
(3)

wherein
Y represents an alkyl group of 1 to 10 carbon atoms, an aryl group of 6 to 15 carbon atoms or an aralkyl group of 7 to 20 carbon atoms, each of which may have substituent(s), or a (2S,3R)-N-tert-butoxycarbonyl-β-aminoepoxide represented by the following general formula

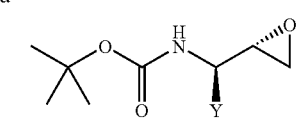
(4)

wherein Y is as defined above, comprising treating, with a base, the (2R,3S)-N-tert-butoxycarbonyl-β-aminoalcohol or (2S,3R)-N-tert-butoxycarbonyl-β-aminoalcohol as produced in accordance with the process of claim 1.

5. The process of claim 2, wherein the diol has 1 to 6 carbon atoms.

6. The process of claim 3, wherein the diol has 1 to 6 carbon atoms.

7. The process of claim 2, wherein the diol is ethylene glycol or 1,3-propanediol.

8. The process of claim 3, wherein the diol is ethylene glycol or 1,3-propanediol.

9. The process of claim 1, wherein the compound of formula (1) or (2) is crystalillized from a diol.

10. The process of claim 9, wherein the diol has 1 to 6 carbon atoms.

11. The process of claim 9, wherein the diol is ethylene glycol or 1,3-propanediol.

12. The process of claim 1, wherein the compound of formula (1) or (2) is crystalillized from a diol-based mixed solvent.

13. The process of claim 12, wherein the diol-based mixed solvent contains a diol and at least one solvent miscible with the diol.

14. The process of claim 13, wherein the solvent miscible with the diol is selected from the group consisting of acetone, 2-butanone, methylisobutylketone, acetonitrile, tetrahydrofuran, methanol, ethanol, 1-propanol, 2-propanol, glycerin and mixtures thereof.

15. A process for producing a (2R,3S)-N-tert-butoxycarbonyl-β-aminoalcohol or a (2S,3R)-N-tert-butoxycarbonyl-β-aminoalcohol which process comprises
dissolving, in a diol or diol-based mixed solvent, a compound represented by formula (1) or (2):

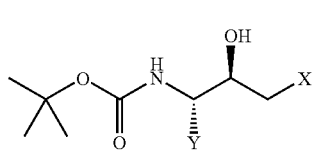
(1)

wherein
Y represents an alkyl group of 1 to 10 carbon atoms, an aryl group of 6 to 15 carbon atoms or an aralkyl group of 7 to 20 carbon atoms, each of which may have substituent(s); and
X represents a halogen atom,

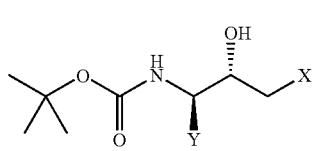
(2)

wherein X and Y are each as defined above, and crystallizing the compound represented by formula (1) or (2) from the resulting solution by addition of water.

16. The process of claim 15, wherein the compound represented by formula (1) is dissolved in a diol or diol-based mixed solvent and crystallized from the resulting solution by the addition of water.

17. The process of claim 15, wherein the compound represented by formula (2) is dissolved in a diol or diol-based mixed solvent and crystallized from the resulting solution by the addition of water.

18. The process of claim 16, wherein the diol has 1 to 6 carbon atoms.

19. The process of claim 17, wherein the diol and the diol has 1 to 6 carbon atoms.

20. The process of claim 16, wherein the diol is ethylene glycol or 1,3-propanediol.

21. The process of claim 17, wherein the diol is ethylene glycol or 1,3-propanediol.

22. The process of claim 15, wherein the compound of formula (1) or (2) is crystalillized from a diol.

23. The process of claim 22, wherein the diol has 1 to 6 carbon atoms.

24. The process of claim 22, wherein the diol is ethylene glycol or 1,3-propanediol.

25. The process of claim 15, wherein the compound of formula (1) or (2) is crystalillized from a diol-based mixed solvent.

26. The process of claim 25, wherein the diol-based mixed solvent contains a diol and at least one solvent miscible with the diol.

27. The process of claim 26, wherein the solvent miscible with the diol is selected from the group consisting of acetone, 2-butanone, methylisobutylketone, acetonitrile, tetrahydrofuran, methanol, ethanol, 1-propanol, 2-propanol, glycerin and mixtures thereof.

28. A process for producing a (2R,3S)-N-tert-butoxycarbonyl-β-aminoepoxide represented by the following general formula (3):

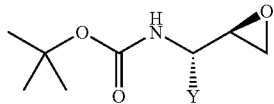
(3)

wherein

Y represents an alkyl group of 1 to 10 carbon atoms, an aryl group of 6 to 15 carbon atoms or an aralkyl group of 7 to 20 carbon atoms, each of which may have substituent(s), or a (2S,3R)-N-tert-butoxycarbonyl-β-aminoepoxide represented by the following general formula

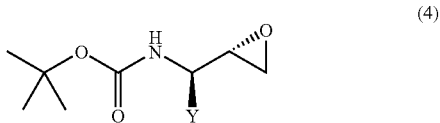
(4)

wherein Y is as defined above, comprising treating, with a base, the (2R,3S)-N-tert-butoxycarbonyl-β-aminoalcohol or (2S,3R)-N-tert-butoxycarbonyl-β-aminoalcohol as produced in accordance with the process of claim 15.

* * * * *